United States Patent [19]

Pasternak et al.

[11] Patent Number: 4,877,529

[45] Date of Patent: Oct. 31, 1989

[54] SEPARATION OF ORGANIC LIQUIDS

[75] Inventors: Mordechai Pasternak, Spring Valley; Craig R. Bartels; John Reale, Jr., both of Wappinger Falls, all of N.Y.

[73] Assignee: Texaco Inc., White Plains, N.Y.

[21] Appl. No.: 222,871

[22] Filed: Jul. 22, 1988

Related U.S. Application Data

[62] Division of Ser. No. 166,575, Mar. 10, 1988, Pat. No. 4,798,674.

[51] Int. Cl.$^4$ .............................................. B01D 13/00
[52] U.S. Cl. .............................. 210/500.37; 210/651; 210/654
[58] Field of Search ....................... 210/500.37, 500.38, 210/500.41, 500.27, 651, 653, 654

[56] References Cited

U.S. PATENT DOCUMENTS 4,728,429 3/1988 Cabasso et al. ................. 210/500.36

Primary Examiner—Frank Sever
Attorney, Agent, or Firm—Robert A. Kulason; James J. O'Loughlin; Carl G. Seutter

[57] ABSTRACT

Mixtures containing methanol and dimethyl carbonate or methanol and methyl t-butyl ether may be treated by pervaporation to cover product containing decreased quantity of methanol.

4 Claims, No Drawings

SEPARATION OF ORGANIC LIQUIDS

This is a division of application Ser. No. 166,575, filed Mar. 10, 1988, now U.S. Pat. No. 4,798,674.

FIELD OF THE INVENTION

This invention relates to the separation of organic liquids. More particularly it relates to treatment of reaction mixtures containing products such as methyl t-butyl ether or dimethyl carbonate to remove methanol therefrom.

BACKGROUND OF THE INVENTION

As is well known to those skilled in the art, it is possible to separate mixtures of liquids by various techniques including adsorption or distillation. These conventional processes, particularly distillation, are however characterized by high capital cost. In the case of distillation for example, the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the charge components form an azeotrope, additional problems may be present which for example, could require that separation be effected in a series of steps (e.g. as in two towers) or by addition of extraneous materials to the system.

There are also comparable problems which are encountered in adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
|---|---|
| Polyvinyl alcohol containing glycerine | Kuraray Co. Japanese Patent 81/193495 (1981) JP 58/g5522A2 (1983) |
| Nafion brand of perfluorosulfonic acid | Cabasso and Liu J. Memb. Sci. 24, 101 (1985) |
| Polytetrafluorethylene film grafted with N—vinyl pyrolidone | Neal, Aptel, and Clement Desalination 53, 297, (1985) |
| Sulfonated polyethylene | Cabasso, Korngold & Liu, J. Pol. Sci.: Letters, 23, 57 (1985) |
| Fluorinated Polyether or Carboxylic Acid Fluorides | U.S. Pat. No. 4,526,948 to DuPont as assignee of Resnickto |
| Selemion AMV blend of Asahi Glass cross-linked styrene butadiene (with quaternary ammonium residues on a polyvinyl chloride backing | Wentzlaff Boddeker & Hattanbach J. Memb. 22,333 (1985) |
| Cellulose triacetate | Wentzlaff, Boddeker & Hattanback, J. Memb. Sci. 22, 333 (1985) |
| Polyacrylontrile or Polytetrafluoroethylene grafted with N—vinyl pyrrolidone | Neel, Aptel & Clement Desalination 53, 297 (1985) |
| Cellulose Acetate and others | Proc. of Int. Mem. Conf. Sept., 1986 Ottawa, p 229 |
| Crosslinked Polyvinyl Alcohol | Eur. Patent 0 096 339 to GFT as assignee of Bruschke |
| Poly(maleimide-acrylonitrile) | Yoshikawa et al J. Pol. Sci. 22, 2159 (1984) |
| Dextrine - isophoronediisocyanate | Chem. Econ. Eng Rev., 17, 34 (1985) |

The cost effectiveness of a membrane is determined by the selectivity and productivity. Of the membranes commercially available, an illustrative membrane of high performance is that disclosed in European patent 0 096 339 A2 of GFT as assignee of Bruschke—published 21 Dec. 1983.

European Patent 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of crosslinked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

See also J. G. Prichard, *Polyvinyl Alcohol, Basic Properties and Uses*, Gordon and Breach Science Publishers, New York (1970) or C. A. Finch, *Polyvinyl Alcohol, Properties and Applications*, John Wiley and Sons, New York (1973).

It is an object of this invention to provide a separation process. Other objects will be apparent to those skilled in the art.

STATEMENT OF THE INVENTION

In accordance with certain of its aspects, this invention is directed to a method of concentrating a charge solution containing (i) an alcohol having less than three carbon atoms and (ii) an oxygenate selected from the group consisting of organic ethers, aldehydes, ketones, and esters which comprises maintaining a non-porous membrane separating layer selected from the group consisting of (i) polyvinyl alcohol which has been crosslinked with an aliphatic polyaldehyde containing at least three carbon atoms including those in said aldehyde groups; and (ii) high molecular weight ion exchange resin in membrane form having carbon atoms in the backbone bearing a pendant acid group, which membrane has been contacted with a quaternary ammonium salt containing four hydrocarbyl groups;

maintaining a pressure drop across said non-porous separating layer;

passing a charge aqueous solution containing (i) an alcohol having less than three carbon atoms and (ii) an oxygenate selected from the group consisting of organic ethers, aldehydes, ketones, and esters into contact with the high pressure side of said non-porous separating layer whereby at least a portion of said alcohol in said charge solution and a lesser portion of oxygenate pass by pervaporation through said non-porous separating layer as a lean mixture containing more alcohol and less oxygenate than are present in said charge solution and said charge solution is converted to a rich liquid containing less alcohol and more oxygenate than are present in said charge solution;

recovering as permeate from the low pressure side of said non-porous separating layer said lean mixture containing more alcohol and less oxygenate than are present in said charge solution, said lean mixture being recovered in vapor phase at a pressure below the vapor pressure thereof; and recovering as retentate from the high pressure side of said non-porous separating layer said rich liquid containing a lower alcohol content and a higher oxygenate content than are present in said charge solution.

DESCRIPTION OF THE INVENTION

The composite structure which may be used in practice of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, bonded strands and characterized by a fabric weight 80±8 grams per square yard, a thickness of 4.2±0.5 mils, a tensile strength (in the machine direction) of 31 psi and (in cross direction) of 10 psi, and a Frazier air permeability of 6 cu.ft./min/sq. ft. @0.5 inches of water.

THE POROUS SUPPORT LAYER

The porous support layer which may be used in practice of this invention is preferably formed of a sheet of polysulfone polymer. Typically the polysulfone may be of thickness of 40–80 microns, say 50 microns and of molecular weight $\overline{M}_n$ of 5,000–100,000, preferably 20,000–60,000 say 40,000. The polysulfone is preferably characterized by a pore size of less than about 500 Å and typically about 200 Å. This corresponds to a molecular weight cut-off of less than about 25,000 typically about 20,000.

The sulfone polymers which may be employed may include those made from cumene, containing isopropylidene groups in the backbone; e.g.

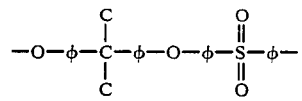

These isopropylidene sulfones containing repeating units including ether-aromatic-isopropylidene-aromatic-ether-aromatic-sulfone-aromatic groups may typically have a molecular weight $\overline{M}_n$ of 15,000–30,000, a water absorption (at 20° C.) of about 0.85 w%, a glass transition temperature of 449° K., a density of 1.25 g/cm$^3$, a tensile strength (at 20° C.) at yield of 10,000 psi, and a coefficient of linear thermal expansion of $2.6 \times 10^{-5}$ mm/mm/°C.

It is found, however, that the preferred sulfone polymers which may be employed in practice of the process of this invention, may include those which are free of isopropylidene moieties in the backbone chain and wherein the phenylene groups in the backbone are bonded only to ether oxygen atoms and to sulfur atoms. One preferred polymer, which may typically, be prepared from

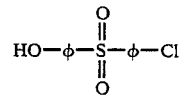

may be characterized by a backbone containing the following repeating groups:

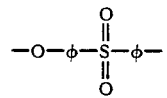

A preferred sulfone polymer may be a polyether sulfone which is free of isopropylidene moieties in the backbone chain and wherein the phenylene groups in the backbone are bonded only to ether-oxygen atoms and to sulfur atoms. This polymer may be characterized by molecular weight $\overline{M}_n$ of 25,000, water absorption @ 20° C. of 2.1 w%, glass transition temperature of 487° K., tensile strength at yield of 12,200 psig at 20° C.; and coefficient of linear thermal expansion of $5.5 \times 10^{-5}$ mm/mm/°C. This polymer has a molecular weight cut off of about 20,000 and has a pore size of about 200 Å.

When the charge contains a component which dissolves the polysulfone (as is the case, e.g. with ketones or esters), the preferred support layer may be a polyacrylonitrile.

THE SEPARATING LAYER

The separating layer which permits attainment of the separation in accordance with this invention may include a non-porous film of cross-linked polyvinyl alcohol of thickness of about 1–10 microns, preferably 1–5 microns, say 3 microns. The layer is formed from polyvinyl alcohol which has been prepared by hydrolysis of polyvinyl acetate-typically 50–100% hydrolyzed, preferably 90–100%, say 100% hydrolyzed. The charge polyvinyl alcohol has a molecular weight of 20,000–200,000, say 115,000. Typically it may be employed as a 5–10 w%, say 7 w% aqueous solution. A commercially available product which may be employed is the Aldrich brand of 100% hydrolyzed polyvinyl alcohol of molecular weight of about 115,000 as a 7 w% aqueous solution.

The membrane or sheet of cross-linked polyvinyl alcohol separating layer is preferably formed in situ on the porous support layer. This is effected by use, as a cross linking agent, of an aliphatic polyaldehyde (preferably a dialdehyde) containing at least three carbon atoms. Preferably the aliphatic dialdehyde may contain 3–8 carbon atoms, most preferably 5 carbon atoms. Typical alphatic dialdehydes which may be employed may include:

TABLE
| |
| --- |
| glutaraldehyde |
| 2-hydroxyhexanedial - 1,6 |
| malonic dialdehyde |
| succinic dialdehyde |
| hexanedial - 1,6 |

The preferred aliphatic dialdehyde is glutaraldehyde. Aldehydes falling outside the scope of this invention typified by formaldehyde, glyoxal, or succinic semialdehyde yield membranes which are characterized by unsatisfactory performance. Performance is judged by the ability of a membrane system to give a high separation factor and high flux. Compositions falling outside the scope of this invention may be characterized by unsatisfactory selectivity or unsatisfactory flux (i.e. productivity) or both.

In situ crosslinking may be carried out by casting 5–10 w%, say 7 w% aqueous solution of polyvinyl alcohol which contains the aliphatic dialdehyde crosslinking agent. The mole ratio of crosslinking agent to polyvinyl alcohol may be 0.05–0.30, say 0.2.

Crosslinking is carried out, in the presence of acid catalyst, preferably inorganic acid. Sulfuric acid is preferred. Hydrochloric acid is much less preferred—because it yields membranes of poor selectivity, although the flux may be high.

It may be possible in one embodiment to crosslink the polyvinyl alcohol separating layer in one step by adding to the aqueous solution of polyvinyl alcohol and dialdehyde, the acid catalyst, preferably sulfuric acid, in mole ratio of acid to dialdehyde of 0.08–0.14, say 0.1.

In another embodiment, it may be possible to apply to the porous support layer, an aqueous mixture of polyvinyl alcohol and dialdehyde. This may be dried at 40° C.–80° C., say 50° C. for 2–10 minutes, say 4 minutes to form a film. There may then be added onto the surface of this film a viscous solution containing 2–7 w%, say 3.5 w% of polyvinyl alcohol and having a mole ratio of sulfuric acid to dialdehyde of 0.08–0.14, preferably 0.1.

The composite membrane, whether prepared by the one-step or the two-step process may then be cured in an oven at 100° C.–200° C., say 125° C. for 1–30 minutes, say 2 minutes to yield a polyvinyl alcohol film having a thickness of 1–10 microns, say 3 microns.

An alternative separating layer which may be employed is a high molecular weight ion exchange resin in membrane form bearing a pendant acid group. The membrane may be formed of a non-porous ion exchange material such as polyolefin (e.g. polyethylene, polypropylene, polystyrene, copolymers of ethylene-propylene, terpolymers of ethylene-propylene-third monomer such as 1,4-hexadiene or dicyclopentadiene or ethylidene norbornene); vinyls such as polyvinyl chloride, polyvinyl acetate, etc., nylons, etc. The molecular weight of the membrane may vary depending on the species. The thickness of the membrane may typically be 130–430 microns, say 190 microns.

The ion exchange resins which may be employed in membrane form are characterized by the presence of a pendant acid group such as a —COOH group or more preferably a —SO$_3$H group. These pendant groups may be introduced into the resin in known manner, if not already present therein, by functionalization with appropriate reagents.

A preferred class of membranes may include those which are perfluorinated (i.e. contain substantially no hydrogen atoms other than those on the pendant acid e.g. —SO$_3$H groups). These membranes may preferably contain —(CF$_2$CF$_2$) and/or

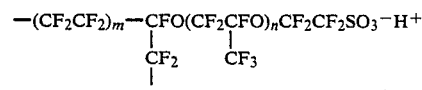

One acid resin membrane which is particularly preferred is that first set forth in the following table which lists illustrative commercially available ion exchange resin membranes which may be employed:

TABLE

A. The Nafion H brand of perfluorinated resin membrane made by DuPont characterized by a thickness of 190 microns having the structure

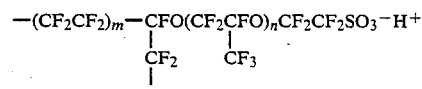

B. The Nafion 901 brand of perfluorinated resin membrane (of thickness about 190 microns) which is characterized by the same general formula as A above except that it also contains —COOH groups in addition to —SO$_3$H groups.

C. Sulfonated polyethylene

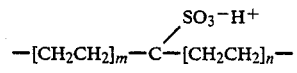

TREATMENT OF THE ION EXCHANGE MEMBRANE

Treatment of the ion exchange membranes to render them useful in the process of the instant invention includes contacting at least the surface which is to contact the charge aqueous dilute solution with a quaternary ammonium salt containing four hydrocarbyl groups. Although both sides of the membrane may be so treated, no advantage is believed to be thereby obtained. Both sides may normally be treated as a matter of convenience in operation.

The quaternary ammonium salt may be characterized by the formula R$_4$NX.

In the above formula, R may be hydrocarbon selected from the group consisting of alkyl, aralkyl, cycloalkyl, aryl, and alkaryl including such radicals when inertly substituted. When R is alkyl, it may be typically be methyl, ethyl, n-propyl, i-propyl, n-butyl, i-butyl, sec-butyl, amyl, octyl, decyl, octadecyl, etc. When R is aralkyl, it may typically be benzyl, beta-phenylethyl, etc. When R is cycloalkyl, it may typically be cyclohexyl, cycloheptyl, cyclooctyl, 2-methylcycloheptyl, 3-butylcyclohexyl, 3-methylcyclohexyl, etc. When R is aryl, it may typically be phenyl, napthyl, etc. When R is alkaryl, it may typically be tolyl, xylyl, etc. R may be inertly substituted i.e. it may bear a non-reactive substituent such as alkyl, aryl, cycloalkyl, ether, etc. Typically inertly substituted R groups may include 2-ethoxybutyl, carboethoxybutyl, 4-methyl cyclohexyl, etc. The preferred R groups may be lower alkyl, i.e. $C_1$-$C_8$ alkyl, groups including e.g. methyl, butyls, amyls, hexyls, octyls, etc. R may preferably be methyl.

The R groups may be different, although preferably they will be the same. X is preferably a halide, preferably chloride or bromide—most preferably bromide. Typical quaternary ammonium salts which may be employed (the first listed being preferred) may include:

TABLE tetramethyl ammonium bromide
tetraoctyl ammonium bromide
tetraheptyl ammonium bromide
tetrahexyl ammonium bromide
tetrapentyl ammonium bromide
tetrabutyl ammonium bromide
tetrabutyl ammonium fluoride
butyl, trioctyl ammonium bromide
tetrapentyl ammonium sulfate, etc.

In practice of the invention, the acid membrane may be treated with the quaternary ammonium salt. The latter may be employed as a 5 w%–50 w%, say, 10 w% solution (corresponding to about 0.2M) in solvent, typically an alcohol such as isopropyl alcohol. Contact may be at 20° C.–40° C. say, 25° for 12–48 hours, say 24 hours with mild agitation. Thereafter, the treated membrane may be washed 2–5, say 3 times for 10–50 minutes, say 30 minutes at 20° C.–40° C., say 25° C. with isopropyl alcohol followed by washes with a 50/50 mixture of isopropanol and water and drying at 20° C.–40° C., say 35° C. for 5–20 minutes, say 10 minutes.

It may be found that treatment of the ion exchange membrane with $R_4NX$ wherein the R group is lower alkyl (i.e. $C_1$-$C_3$, preferably methyl) gives outstanding results in terms of Separation and Flux.

THE PERVAPORATION MEMBRANE

It is a feature of this invention that the composite membrane used in the process of this invention may typically comprise (i) an optional carrier layer, characterized by porosity and mechanical strength, for supporting a porous support layer and a separating layer, (ii) a preferred polysulfone porous support layer of molecular weight of 5,000–100,000, of thickness of 10–80 microns, and of molecular weight $\overline{M}n$ cut off of 25,000–100,000, and (iii) as a non-porous separating layer either (a) polyvinyl alcohol of molecular weight of 20,000–200,000 which has been crosslinked with an aliphatic dialdehyde containing 3–8 carbon atoms or (b) a high molecular weight ion exchange resin in membrane form bearing a pendant acid group which membrane has been contacted with a quaternary amonium salt containing four hydrocarbyl groups.

When the charge solution contains a component in which, the polysulfone is soluble (e.g. a ketone or an ester), then the preferred support layer may be a polyacrylonitrile.

The membranes of this invention may be utilized in various configurations. It is, for example, possible to utilize the composite in a plate-and-frame configuration in which separating layers may be mounted on the porous support layer with the carrier layer.

It is possible to utilize a spiral wound module (in the case of a supported membrane) which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There is then placed on one face of the bag-like unit, adjacent to the separating layer, and coterminous therewith, a feed channel sheet—typically formed of a plastic foraminous net.

The so-formed assembly is wrapped around a preferably cylindrical conduit which bears a plurality of perforations in the wall—preferably in a linear array which is as long as the width of the bag-like unit. The projecting portion of the discharge channe of the bag-like unit is placed over the perforations of the conduit; and the bag-like unit is wrapped around the conduit to form a spiral wound configuration. It will be apparent that, although only one feed channel is present, the single feed channel in the wound assembly will be adjacent to two faces of the membrane layer. The spiral wound configuration may be formed by wrapping the assembly around the conduit a plurality of times to form a readily handlable unit. The unit is fitted within a shell (in manner comparable to a shell-and-tube heat exchanger) provided with an inlet at one end and an outlet at the other. A baffle-like seal between the inner surface of the shell and the outer surface of the spiral-wound unit input prevents fluid from bypassing the operative membrane system and insures that fluid enters the membrane system principally at one end. The permeate passes from the feed channel, into contact with the separating layer and thence therethrough, into the permeate channel and thence therealong to and through the perforations in the conduit through which it is withdrawn as net permeate.

In the case of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fibre. In this embodiment, the porous support (e.g. polysulfone) layer may be extruded or spun as a fine tube with a wall thickness of typically 0.0001–0.1 mm. The extruded tubes are passed through a bath of polyvinyl alcohoL which is cross-linked and cured in situ on the tubes. A bundle of these tubes is secured (with an epoxy adhesive) at each end in a header; and the fibres are cut so that they are flush with the ends of the header. This tube bundle is mounted within a shell in a typical shell-and-tube assembly.

Whenever the perfluorinated resin is used in the form of hollow fibres, it may be similarly mounted in a shell.

In operation, the charge liquid may be admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and (in the case of e.g. polyvinyl alcohol) the separating layer may be extruded and thereafter crosslinked and cured in situ prior to mounting in the headers.

PERVAPORATION

It is a feature of the non-porous polyvinyl alcohol or ion exchange membrane separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exists as a vapor may be recovered by condensing at low temperature or alternatively may be swept away by use of a moving stream of gas. The discharge side of the membrane is maintained at a pressure which is less than the vapor pressure of the permeate. Preferably, the permeate side of the membrane is maintained at a low pressure, typically 5–10 mm. Hg.

For general background on pervaporation, note U.S. Pat No. 4,277,344; U.S. Pat. No. 4,039,440; U.S. Pat. No. 3,926,798; U.S. Pat. No. 3,950,247; U.S. Pat. No. 4,035,291; etc.

It is a feature of this invention that the novel membrane may be particularly useful in pervaporation processes for concentrating a charge solution containing (i) an alcohol and (ii) oxygenate selected from the group consisting of organic ethers, aldehydes, ketones, and esters.

The oxygenate may be (i) an organic ether such as dimethyl ether, diethyl ether, di-n-propyl ether, di-n-butyl ether, methyl t-butyl ether, ethyl t-butyl ether, methyl t-amyl ether, ethyl t-amyl ether, etc.;

(ii) an aldehyde such as acetaldehyde, propionaldehyde, butyraldehyde, benzaldehyde, etc.;

(iii) a ketone such as acetone, methyl ethyl ketone, diethyl ketone, etc.; or (iv) an ester such as methyl acetate, methyl propionate, methyl butyrate, methyl benzoate, dimethyl carbonate, diethyl carbonate, etc.

The alcohol may typically be methanol, ethanol, n-propanol, i-propanol, butanols, pentanols, hexanols, etc.

Most favorable results may be obtained with the water-soluble lower alkanols, most preferably methanol.

It will be obvious to those skilled in the art that the process of this invention may find particular use when the charge mixture to be treated is a reaction product wherein one of the components to be separated is unreacted charge component. A typical such charge mixture is that attained from the reaction of methanol and carbon monoxide wherein the mixture may contain unreacted methanol and product dimethyl carbonate (DMC). Another illustrative charge mixture is that attained from the reaction of methanol and isobutene wherein the reaction mixture may contain methanol and methyl t-butyl ether (MTBE).

These charge solutions may have been subjected to preliminary separation, e.g. distillation, to yield, for example, an azeotrope of methanol and dimethyl carbonate.

Other charge solutions may include (i) methyl acetate-methanol, (ii) ethyl acetate-ethanol, etc.

In practice of the pervaporation process of this invention, the charge solution typically at 40° C.–120° C., say 70° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 0.5–50 preferably 5–20, say 1.5 mm.Hg, or lower.

The permeate which passes through the membrane typically includes e.g. methanol and a small proportion of the oxygenate from the charge liquid. Typically, the permeate contains 90–99 w%, say up to 99 w% methanol. Permeate is recovered in vapor phase.

Pervaporation may typically be carried out at a flux of 0.01–1.5, say about 1.0 kilograms per square meter per hour (kmh). Typically, the units may have a selectivity (measured in terms of w% of e.g. methanol in the permeate during pervaporation at 70° C. of a ca 30 w% solution of oxygenate through a standard polyvinyl alcohol separating layer of 3 microns thickness) of 90–99.9 w% methanol. It will vary depending on the oxygenate.

Practice of the process of this invention will be apparent to those skilled in the art from inspection of the following examples wherein, as elsewhere in this specification, all parts are parts by weight unless otherwise stated.

DESCRIPTION OF SPECIFIC EMBODIMENTS

In the Examples, the following membrane systems are employed:

A. Polyvinyl alcohol—the porous support is a polyester carrier layer which includes a plurality of nonwoven, bonded strands, characterized by a fabric weight of about 80 grams per square yard, a thickness of about 4.2 mils, a tensile strength (in the machine direction) of about 31 psi and (in cross 10 direction) of 10 psi, and a Frazier air permeability of about 6 cu.ft./min./sq.ft. at 0.5 inches of water.

The support layer, bonded to the carrier layer, is an isoproylidene sulfone polymer. The polymer has a molecular weight $\overline{M}n$ of 25,000, a water absorption at 20° C. of 0.85 w%, a glass transition temperature of 449° K., a tensile strength at yield of 10,000 psig at 20° C., a coefficient of linear thermal expansion of $2.6 \times 10^{-5}$ mm/mm/°C.; a pore size of about 200 Å, and a molecular weight cutoff of about 20,000.

The separating layer is formed from a 7 w% aqueous solution of Aldrich brand of 100% hydrolyzed polyvinyl alcohol (PVA) of molecular weight $\overline{M}_n$ of about 115,000. This layer is crosslinked (during casting on the bonded support layer-carrier layer assembly) by mixing with a 25 w% aqueous solution of glutaraldehyde crosslinking agent (in mole ratio of agent to PVA repeat unit of 0.2) in the presence of 0.5N sulfuric acid, at mole ratio of acid to glutaraldehyde of 0.1. (10 g of 7 w% aqueous solution of polyvinyl alcohol plus 1.37 g of 25 w% aqueous solution of glutaraldehyde plus 1.19 g of 0.5N sulfuric acid). The composite is then cured for 3 minutes at 190° C. to yield a film three microns thick.

B. Polyvinyl alcohol—the procedure of A is followed except that the membrane is cured at 125° C. for 15 minutes.

C. Polyvinyl alcohol—the procedure of A is followed except that the membrane is cured at 125° for 8 minutes.

D. Polyvinyl alcohol—the procedure of A is followed except that the polyvinyl alcohol separating layer is laid down in two steps. In the first step, 10 g of a 7 w% solution of polyvinyl alcohol (100% hydolyzed) containing 1.37 g of glutaraldehyde (25 wt % aqueous solution) is cast as a 4 mil film on the polysulfone (m.w. cutoff 40,000) support. This is then cured at 50° C. for 4 minutes. In the second step, 10 g of a 3.5 w% polyvinyl alcohol (100% hydolyzed) containing 1.19 g of 0.5N sulfuric acid is cast as 4 mil film (on top of the cured first film. The assembly is then cured at 125° C. for 8 minutes.

E. Polyvinyl alcohol—the procedure of A is followed except that the polyvinyl alcohol separating layer is laid down is two steps. In the first step, 10 g of a 7 w% solution of polyvinyl alcohol (100% hydrolyzed) containing 1.67 g of 2-hydroxyhexanedial-1,6 (25 wt % aqueous solution) is cast as a 4 mil film on polysulfone (m.w. cutoff 20,000) support. This is then cured at 50° C. for 5 minutes. In the second step, 10 g of a 3.5 w% polyvinyl alcohol (100% hydrolyzed) containing 1.19 g 0.5N sulfuric acid is cast as a 4 mil film (on top of the cured first film). The assembly is then cured at 125° C. for 15 minutes.

F. Polyvinyl alcohol—the procedure of E is followed except that 0.46 g glyoxal (40 wt % aqueous solution) is substituted for the 1.67 g of 2-hydroxyhexanedial-1,6.

G. Polyvinyl alcohol—the procedure of A is followed except that (i) 0.092 g of maleic acid is used in place of 1.37 g of glutaraldehyde, (25 wt% aqueous solution) (ii) no sulfuric acid is added, and (iii) the membrane is cured at 150° C. for 2.5 minutes instead of 190° C. for 3 minutes.

H. Polyvinyl alcohol—the procedure of A is followed except that (i) 0.92 g of formaldehyde (37 w% aqueous solution) is used in place of 1.37 g of glutaraldehyde, (ii) 0.42 g of 0.5N hydrochloric acid is used in place of 1.19 g of 0.5N sulfuric acid, and (iii) the membrane is cured at 150° C. for 2.5 minutes instead of 190° C. for 3 minutes.

I. Polyvinyl alcohol—The membrane employed is a commercially available cross-linked polyvinyl alcohol marketed by Gesellschaft fur Trenntechnik (GFT) Gmbh prepared according to European Patent 0 096 339 A2.

J. Fluorinated Resin—The Nafion-H 117 brand of perfluorinated resin membrane of DuPont having a thickness of 190 microns and having the formula

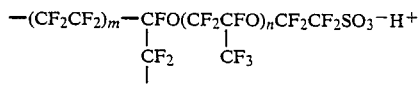

This membrane is treated with, as quaternary, tetramethyl ammonium bromide by immersion in a 0.2 molar solution in isopropanol at 25° C. for 24 hours, followed by three washes at 25° C. for 30 minutes each with isopropyl alcohol and three washes at 35° C. for 30 minutes with 50/50 w water-isopropanol. This membrane system did not include support layer or carrier layer.

K. Fluorinated Resin—the procedure of J is followed except that the quaternary is tetrabutyl ammonium bromide L. Fluorinated Resin—the procedure of J is followed except that the quaternary is tetra n-hexyl ammonium bromide.

M. Fluorinated Resin—the procedure of J is followed except that the quaternary is tetra n-octyl ammonium bromide.

N. Fluorinated Resin—the procedure of J is followed using the Nafion-H 117 brand of DuPont Resin. No quaternary is employed in N.

EXAMPLE I

In this example, which represents the best mode presently known of separating methanol from dimethyl carbonate by the process of this invention, the selective separating layer is the membrane A system supra.

The membrane is evaluated in a pervaporation cell to which the charge at 70° C. is a solution rich in methanol and lean in dimethyl carbonate (approximately an azeotropic mixture). Permeate pressure is 1.0 mm Hg. The permeate condenser contains 93.5 w% methanol. The Separation Factor S is 9.6 and the Flux is 1.13 kmh (kilograms per square meter per hour).

EXAMPLES II–IV

In this series of Examples, the charge, enriched in methanol and lean in dimethyl carbonate is passed at 70° C. through various membranes; and the Separation Factor S and the Flux F (kilograms per square meter per hour) are noted together with the concentration (w%) of methanol in the permeate):

TABLE 1

| Example | Membrane | Feed % MeOH | Feed % DMC | Feed % Water | Permeate % MeOH | S | F |
|---|---|---|---|---|---|---|---|
| II | A | 72.8 | 26.9 | 0.4 | 93.5 | 9.60 | 1.13 |
| III | B | 67.9 | 32.1 | 0 | 97.5 | 18.75 | 0.10 |
| IV | C | 73.1 | 26.5 | 0.4 | 94.3 | 11.4 | 0.48 |

From the above table, it is apparent that the performance of the polyvinyl alcohol membrane system is a function of the curing conditions.

EXAMPLES V–IX

In this series of Examples, the procedure of Examples II–IV is followed except that different membranes are employed.

TABLE 2

| Example | Membrane | Feed % MeOH | Feed % DMC | Feed % Water | Permeate % MeOH | S | F |
|---|---|---|---|---|---|---|---|
| V | J | 72.4 | 27.2 | 0.4 | 89.4 | 3.6 | 0.60 |
| VI | K | 73.2 | 26.5 | 0.3 | 85.9 | 2.4 | 0.55 |
| VII | L | 72.6 | 27.1 | 0.3 | 80.9 | 1.6 | 1.35 |
| VIII | M | 72.7 | 27 | 0.3 | 77.9 | 1.35 | 1.22 |
| IX | N | 73.1 | 26.6 | 0.3 | 86.7 | 2.6 | 0.14 |

From this table, it is apparent that as the length of the hydrocarbon substituent (over the rage of C-1 to C-8) on the quaternary ammonium cation decreases, the separation factor S increases.

EXAMPLES X-XV

In this series of Examples, the procedure of Examples II–IV is followed using different membrane systems. The concentration of methanol in the feed varies over a narrow range.

TABLE 3

| Example | Membrane | Feed % MeOH | Permeate % MeOH | S | F |
|---|---|---|---|---|---|
| X | A | 72.8 | 93.5 | 9.60 | 1.13 |
| XI | E | 69.6 | 98.4 | 26.90 | 0.04 |
| XII | F | 71.2 | 90.2 | 3.7 | 0.016 |
| XIII | G | 70.8 | 89.6 | 3.6 | 0.057 |
| XIV | H | 71.5 | 79.5 | 1.5 | 0.035 |
| XV | I | 69.5 | 89.2 | 3.6 | 0.010 |

From the above table, it is apparent that the polyvinyl alcohol membranes which are cross linked with dialdehydes having greater than three carbon atoms show better separation and flux when used with a charge containing methanol, dimethyl carbonate, and water. Furthermore, the membranes of Examples X-XIV (i.e. membranes A, E, F, G, and H) perform much better than the commercially available membrane I of Example XV.

EXAMPLES XVI-XVIII

In this series of Examples, the procedure of Examples II–IV is followed except that the charge stream contains methanol and methyl t-butyl ether.

TABLE 4

| Example | Membrane | Feed % MeOH | Feed % MTBE | Permeate % MeOH | S | F |
|---|---|---|---|---|---|---|
| XVI | A | 67.9 | 32.1 | 99.9 | 472 | 1.0 |
| XVII | D | 81.1 | 18.9 | 99.9 | 233 | 0.43 |
| XVIII* | I | 81.1 | 18.9 | — | — | 0 |

From the above table, it is apparent that Examples XVI-XVII using the membranes of this invention permit attainment of satisfactory separation while the membrane (which has not been crosslinked) of Example XVIII does not permit any separation at all.

EXAMPLES XIX-XX

In this series of Examples, the procedure of Examples XVI-XVIII is followed. The charge contains less methanol and more MTBE. Example XIX is carried out at 70° C.; Example XX at 28° C.

TABLE 5

| Example | Membrane | Feed % MeOH | Permeate % MeOH | S | F |
|---|---|---|---|---|---|
| XIX | A | 18.07 | 61.55 | 7.26 | 0.008 |
| XX | D | 13.20 | 99.62 | 1730 | 0.004 |

EXAMPLES XXI-XXV

TABLE 6

| Example | Membrane | R | Feed % MeOH | Permeate % MeOH | S | F |
|---|---|---|---|---|---|---|
| XXI | J | 1 | 69.36 | 99.74 | 169 | 0.4 |
| XXII | K | 4 | 69.38 | 99.5 | 87.8 | 0.32 |

TABLE 6-continued

| Example | Membrane | R | Feed % MeOH | Permeate % MeOH | S | F |
|---|---|---|---|---|---|---|
| XXIII | L | 6 | 76.56 | 97.61 | 12.5 | 0.68 |
| XXIV | M | 8 | 81.55 | 95.66 | 5.0 | 0.76 |
| XXV | N | — | 72.45 | 99.8 | 189 | 0.0 |

From this table, it is apparent that as the length of the hydrocarbon subsituent on the quaternary ammonium cation decreases (over the range R of C-1 to C-8), the separation factor S increases.

EXAMPLES XXVI-XXVIII

In this series of Examples, the procedure of Examples XXI-XXV is followed using a feed containing less methanol and more methyl t-butyl ether. Examples XXVI and XXVIII are carried out at 70° C. Example XXVII is carried out at 28° C.

TABLE 7

| Example | Membrane | Feed % MeOH | Permeate % MeOH | S | F |
|---|---|---|---|---|---|
| XXVI | J | 16.93 | 91.2 | 50.9 | 0.02 |
| XXVII | K | 11.51 | 97.8 | 348 | 0.05 |
| XXVIII | M | 15.56 | 48.25 | 4.7 | 0.23 |

It is believed that the polyvinyl alcohol membrane is preferred when separating DMC and methanol (Example I). When treating charge containing a low concentration of MTBE and a high concentration of methanol (Example XVI), the polyvinyl alcohol membrane is preferred.

However, when the charge contains a high concentration of MTBE and a low concentration of methanol, the preferred membrane may be an ion exchange membrane (Example XXVII).

It will be apparent that with the preferred systems, the Separation is high and the Flux is good.

Although this invention has been illustrated by reference to specific embodiments, it will be apparent to those skilled in the art that various changes and modifications may be made which clearly fall within the scope of this invention.

We claim:

1. A non-porous ion exchange membrane comprising A molecular structure enabling concentration of a charge solution containing (i) an alcohol having less than three carbon atoms and (ii) an oxygenate selected from the group consisting of organic ethers, aldehydes, ketones, and esters, including a high molecular weight perfluorinated non-porous ion exchange acid resin in membrane form having carbon atoms in the backbone, bearing a pendant acid group, said membrane having been contacted with a quaternary ammonium salt containing hydrocarbyl groups each of which contains less than four carbon atoms.

2. A non-porous ion exchange membrane as claimed in claim 1 where said pendant acid group is —SO$_3$H.

3. A non-porous ion exchange membrane as claimed in claim 1 wherein said perfluorinated resin contains the structure

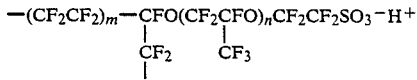

4. A non-porous ion exchange membrane as claimed in claim 1 wherein said quaternary ammonium salt is R$_4$NBr wherein R is methyl.

* * * * *